US005955496A

United States Patent [19]
Hammock et al.

[11] Patent Number: 5,955,496
[45] Date of Patent: Sep. 21, 1999

[54] DIHYDROXY-OXY-EICOSADIENOATES

[75] Inventors: Bruce D. Hammock, Davis, Calif.; Mehran F. Moghaddam, Wilmington, Del.; Jeffrey M. Cheek, Sacramento, Calif.; Babak Borhan, New York, N.Y.; James Fergusson, Davis, Calif.; David F. Grant, Little Rock, Ak.; Jessica F. Greene, Davis, Calif.; Kazuhiko Matoba, Osaka, Japan; Jiang Zheng; Marlene F. Sisemore, both of Davis, Calif.

[73] Assignee: The Regents of the University of California, Oakland, Calif.

[21] Appl. No.: 08/909,523

[22] Filed: Aug. 12, 1997

Related U.S. Application Data

[60] Provisional application No. 60/023,397, Aug. 13, 1996.
[51] Int. Cl.[6] .......................... A61K 31/34; C07D 307/12
[52] U.S. Cl. .............................................. 514/473; 549/475
[58] Field of Search .............................. 514/473; 549/475

[56] References Cited

U.S. PATENT DOCUMENTS

| | | | |
|---|---|---|---|
| 4,088,779 | 5/1978 | Vlattas | 424/285 |
| 5,445,956 | 8/1995 | Hammock et al. | 435/195 |
| 5,455,271 | 10/1995 | Yuan et al. | 514/538 |
| 5,488,033 | 1/1996 | Wei | 514/12 |
| 5,504,111 | 4/1996 | Flavin et al. | 514/530 |
| 5,530,114 | 6/1996 | Bennett et al. | 536/24.3 |
| 5,593,990 | 1/1997 | D'Amato | 514/235.2 |

OTHER PUBLICATIONS

Bone, "Toward an Epidemiology and Natural History of SIRS (Systemic Inflammatory Response Syndrome)," *JAMA*, 268:24, pp. 3452–3455 (Dec. 23/30, 1992).

Borhan et al., "Stereochemical Aspects of Cytosolic Epoxide Hydrolase Hydration of Methyl Diepoxystearates," *Tetrahedron*, 49:13, pp. 2601–2612(1993).

Borhan et al., "Improved Radiolabeled Substrates for Soluble Epoxide Hydrolase," *Analytical Biochemistry*, 231, pp. 188–200 (1995).

Cheek et al., "Ozone Injury to Alveolar Epithelium in Vitro Does Not Reflect Loss of Antioxidant Defenses," *Toxicology and Applied Pharmacology*, 125, pp. 59–69 (1994).

Demling, "The Modern Version of Adult Respiratory Distress Syndrome," *Annu. Rev. Med.*, 46, pp. 193–202 (1995).

Dietze et al., "Inhibition of Cytosolic Epoxide Hydrolase by trans–3–Phenylglycidols," *Biochemcial Pharmacology*, 42:6, pp. 1163–1175 (1991).

Dietze et al., "Spectrophotometric Substrates for Cytosolic Epoxide Hydrolase," *Analytical Biochemistry*, 216, pp. 176–187 (1994).

Dobbs et al., "An Improved Method for Isolating Type II Cells in High Yield and Purity,"*Am. Rev. Resp. Dis.*, 134, pp. 141–145 (1986).

Grant et al., "Development of and In Situ Toxicity Assay System Using Recombiant Baculoviruses," *Biochemical Pharmacology*, 51, pp. 502–515 (1996).

Grnykiewicz et al., "A New Generation of $Ca^{2+}$ Indicators with Greatly Improved Fluorescence Properties," *J. Biological Chemistry*, 260:6, pp. 3440–3450 (Mar. 25, 1985).

Ingram, R.H. Jr., *Harrison's Principals of Internal Medicine*, 13, p. 1240 (1995).

Miyamoto et al., "Inhibition of Epoxide Hydrolases and Glutathione S–Transferases by 2–,3–, and 4–Substituted Derivatives of 4'–Phenylchalcone and its Oxide," *Arch. Biochem. & Biophys.*, 254, pp. 203–213 (Apr. 1987).

Mullin and Hammock, "Chalcone Oxides —Potent Selective Inhibitors of Cytosolic Epoxide Hydrolase,"*Archives of Biochemistry and Biophysics*, 216:2, pp. 423–439 (Jul. 1982).

Witrom and Hammock, "Continuous Spectrophotometric Assays for Cytosolic Epoxide Hydrolase," *Analytical Biochemistry*, 174, pp. 291–299 (1988).

Moghaddam et al., "Bioactivation of Leukotoxins to Their Toxic Diols by Epoxide Hydrolase," *Nature Medicine*, 3(5), May 1997, pp. 562–566.

Moghaddam et al., "Novel Metabolic Pathways for Linoleic and Arachidonic Acid Metabolism," *Biochimica et Biophysica Acta*, 1290, 1996, pp. 327–339.

*Primary Examiner*—Phyllis G. Spivack
*Attorney, Agent, or Firm*—Majestic, Parsons, Siebert & Hsue

[57] ABSTRACT

The present invention provides novel biologically active tetrahydrofuran diols of arachidonic acid.

8 Claims, 3 Drawing Sheets

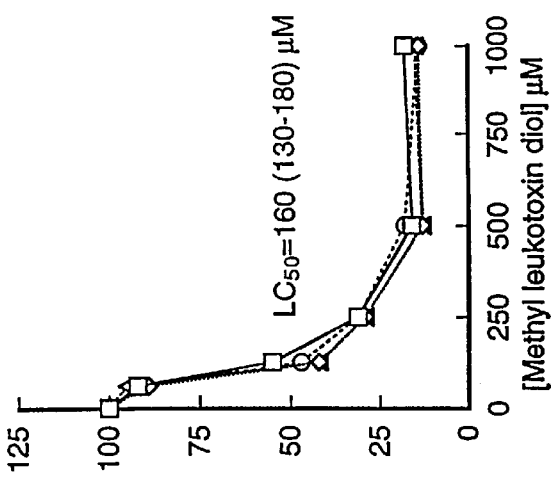
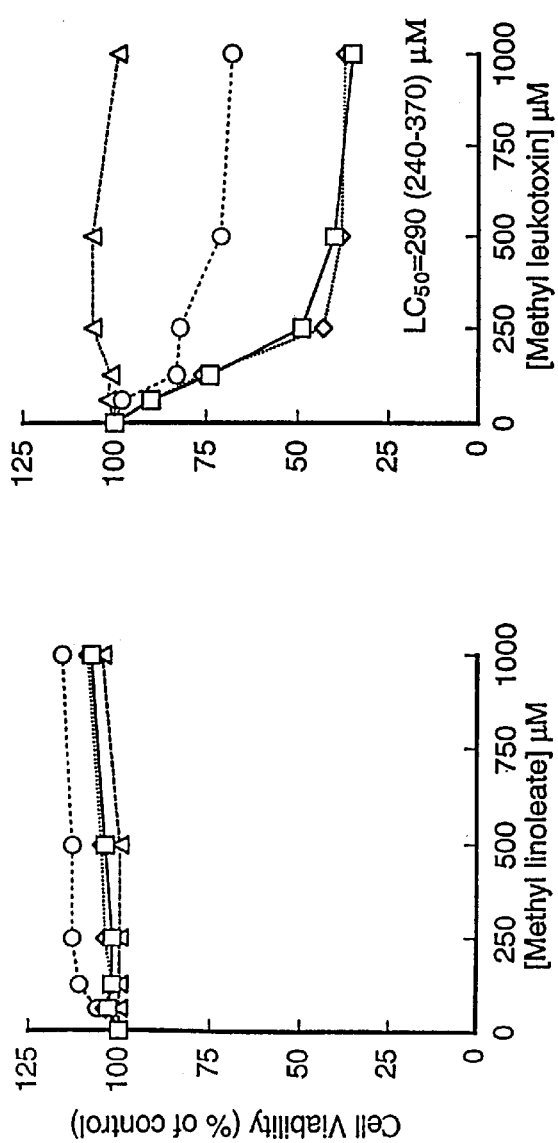
FIGURE 2A  FIGURE 2B  FIGURE 2C

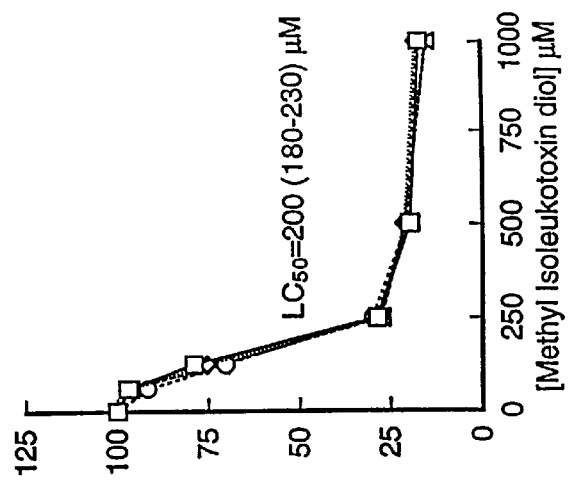
FIGURE 2E
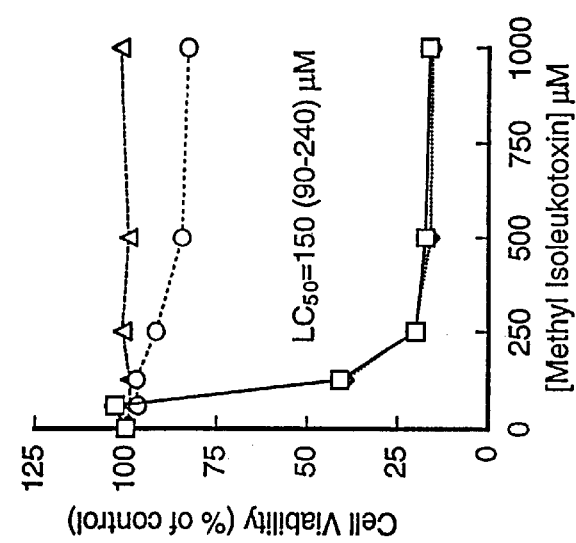
FIGURE 2D
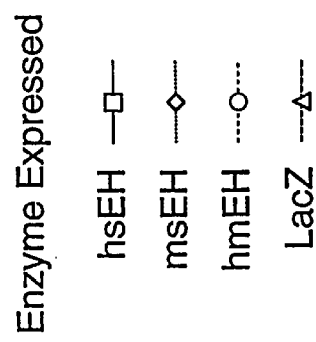

_DIHYDROXY-OXY-EICOSADIENOATES_

This application claims the benefit of U.S. Provisional Application Ser. No. 60/023,397, filed Aug. 13, 1996.

This invention was made with Government support under Grant ES02710, awarded by the National Institutes of Health. The Government has certain rights in this invention.

FIELD OF THE INVENTION

The present invention generally relates to treating inflammatory conditions, such as adult respiratory distress syndrome (ARDS), and other acute inflammatory conditions, such as systemic inflammatory response syndrome (SIRS), and more particularly to methods of treating inflammatory diseases mediated by polyunsaturated lipid metabolites by inhibiting epoxide hydrolase, to methods for assaying or screening epoxide hydrolase inhibitors for toxicity, and methods for the analysis of metabolites of lipid metabolites as indicators of oxidative stress and disease states. The invention also includes as one aspect novel biologically active tetrahydrofuran diols of arachidonic acid (dihydroxy-oxy-eicosadienoates or DiHOxyEDEs).

BACKGROUND OF THE INVENTION

Inflammation is signaled by redness, swelling, heat and pain as a reaction of the body against injury or assault. A variety of chemicals have been implicated as chemical mediators of the inflammatory reaction, including histamine, kinins, prostaglandins, platelet-activating factors, leukotrienes, and, from nerve endings, substance P. Mediators of the acute inflammatory reaction seem to play roles in one or more of increasing vascular permeability, attracting leukocytes, producing pain, local edema and necrosis.

The inflammatory response is one of the most important physiological mechanisms for the maintenance of human health. However, disorders of inflammation or an inappropriate inflammatory response can result in tissue injury, morbidity, or mortality.

Swelling is a characteristic inflammatory response of tissues to injury. Swelling is produced by leakage of water and solutes of the blood directly into the tissue matrix. The increased leakiness of blood vessels after injury may be due to direct damages of blood vessels or may occur after the release of substances such as histamine (inflammatory mediators) that open up gaps between endothelial cells that line the blood vessels. These and other inflammatory signals can act directly on leukocytes leading to their attachment to the walls of blood vessels, a change in leukocyte morphology, and movement through the wall of the vessel into the tissues. A mild degree of swelling (or edema) does not affect the functional integrity of injured tissues (except perhaps in the brain), but, in severe injuries, massive swelling distorts tissue architecture, impedes the delivery of oxygen to cells, and causes extensive fluid loss from the vascular compartment.

Inflammation is also involved in various chronic conditions, such as asthma, although it is not presently clear which inflammatory cells or which particular mediators are significantly involved in asthma.

Adult respiratory distress syndrome (ARDS) is a pulmonary disease that has a mortality rate of 50% and results from lung lesions that are caused by a variety of conditions found in trauma patients and in severe burn victims. Ingram, R. H. Jr., "Adult Respiratory Distress Syndrome," _Harrison's Principals of Internal Medicine_, 13, p. 1240, 1995. With the possible exception of glucocorticoids, there have not been therapeutic agents known to be effective in preventing or ameliorating the tissue injury, such as microvascular damage, associated with acute inflammation that occurs during the early development of ARDS.

ARDS, which is defined in part by the development of alveolar edema, represents a clinical manifestation of pulmonary disease resulting from both direct and indirect lung injury. While previous studies have detailed a seemingly unrelated variety of causative agents, the initial events underlying the pathophysiology of ARDS is not well understood. ARDS was originally viewed as a single organ failure, but is now considered a component of the multisystem organ failure syndrome (MOFS). Pharmacologic intervention or prevention of the inflammatory response is presently viewed as a more promising method of controlling the disease process than improved ventilatory support techniques. See, for example, Demling, _Annu. Rev. Med._, 46, pp. 193–203, 1995.

Another disease (or group of diseases) involving acute inflammation is the systematic inflammatory response syndrome, or SIRS, which is the designation recently established by a group of researchers to describe related conditions resulting from, for example, sepsis, pancreatitis, multiple trauma such as injury to the brain, and tissue injury, such as laceration of the musculature, brain surgery, hemorrhagic shock, and immune-mediated organ injuries. Bone, _JAMA_, 268:24, pp. 3452–3455, 1992.

U.S. Pat. No. 5,504,111, inventors Falvin et al., issued Apr. 2, 1996, suggests use of 2,3-alkylcarbonyloxybenzoic acid in treating ARDS. The patentees suggest a use for their invention is also in the therapeutic treatment and/or prevention of sepsis and septic shock because many of the physiological and, indeed, the pathological processes involved with ARDS have also been demonstrated to be involved in the condition of sepsis and septic shock.

U.S. Pat. No. 5,488,033, inventor Wei, issued Jan. 30, 1996, discloses treatments with corticotropin-releasing factor as being useful in systemic inflammatory conditions such as SIRS, when such are characterized by vascular leakage, by suppressing such vascular leakage.

U.S. Pat. No. 5,455,271, issued Oct. 3, 1995, inventors Yuan et al., discloses inhibitors of leukotriene $A_4$ hydrolase. This metaloprotein hydrolase is said to exhibit inhibition of both epoxide hydrolase and aminopeptidase activities. The patent suggests that selective inhibitors of LTA4 hydrolase are of interest as potential anti-inflammatory agents. The patent discloses a class of transition state analog inhibitors based on the proposed mechanism of the aminopeptidase activity and the natural substrate structure of the LTA4 hydrolase enzyme.

U.S. Pat. No. 5,530,114, issued Jun. 25, 1996, inventors Bennett et al., discloses methods of treating diseases amendable to modulation of the synthesis or metabolism of arachidonic acid by providing anti-sense oligonucleotides capable of inhibiting the function of RNA encoding proteins involved in the synthesis and metabolism of arachidonic acid and related compounds. In particular, various of the leukotrienes resulting from an oxidative pathway (the lipoxygenase pathway) are discussed.

SUMMARY OF THE INVENTION

In one aspect of the present invention, a method for treating inflammatory diseases, particularly adult respiratory distress syndrome (ARDS), is provided which comprises administering to a patient in need of therapy an effective therapeutic amount of an epoxide hydrolase inhibitor.

Aspects of the invention generally relate to our discovery that the diol metabolite of linoleate appears to lead to ARDS symptoms and to increase inflammation. Accordingly, an aspect of the invention is for treatments by means of drugs that inhibit formation of leukotoxin and leukotoxin diol, hydrolase) of leukotoxin that is toxic to pulmonary and vascularepithelium and other cell types associated with ARDS and related disorders. It is likely that diol metabolites account for many of the biological effects attributed to the leukotoxins.

SCHEME 1

Linoleic Acid
(Octadeca-9(z), 12(z)-dienoic Acid)

[O] or P450 Monoxygenase

Isoleukotoxin
(cls-12,13-Epoxyoctadec-9(Z)-enoic Acid)

Leukotoxin
(cls-9,10-Epoxyoctadec-9(Z)-enoic Acid)

$H^+$ or Epoxide Hydrolase

Isoleukotoxin Diol
(threo-12,13-Dihydroxyoctadec-9(Z)-enoic Acid)

Leukotoxin Diol
(threo-9,10-Dihydroxyoctadec-12(Z)-enoic Acid)

which drugs include epoxide hydrolase inhibitors such as chalcone oxides, lipid alkoxides, glycidols, and diimides, or by treating the inflammation (caused by leukotoxin diol) by means of THF-diols of an arachidonate, which act in an anti-inflammatory manner. More particularly, the administered epoxide hydrolase inhibitor retards or prevents an inflammatory response in a patient via an inhibition of formation of one or more polyunsaturated lipid metabolites. For example, the administering is effective to inhibit the formation of one or more dihydroxy-oxy-eicosadienoates, or DiHOxyEDEs in the arachidonic acid series of oxylipins, the leukotoxin diols in the linoleaic acid series, or other lipid diols including tetrahydrofuran diols.

The art has up to now viewed leukotoxin, or cis-9,10-epoxyoctadec-12(Z)-enoic acid, as being the agent causing the toxic responses characterized by ARDS due to its presence in skin and plasma of such patients. Leukotoxin and isoleukotoxin (cis-9,10-epoxyoctadec-12(Z)-enoic acid and cis-12,13-epoxyoctadec-9(Z)-enoic acid) are monoepoxides of linoleic acid (octadeca-9(Z),12(Z)-dienoic acid), an essential fatty acid found naturally in vegetable oils and animal fats. In the body, linoleic acid is activated to the regioisomers of leukotoxin and isoleukotoxin by cytochrome P-450 and other oxidative pathways, then metabolized to the corresponding dihydroxy compounds, leukotoxin diol (cis9,10-dihydroxyoctadec-12(Z)-enoic acid or 9,10-DiHODE) and isoleukotoxin diol (cis-12,13-dihydroxyoctadec-9(Z)-enoic acid or 12,13-DiHODE) by epoxide hydrolase. This reaction is carried out by the microsomal epoxide hydrolase (mEH) and soluble epoxide hydrolase (sEH) with the soluble enzyme being of greater importance.

Surprisingly, our studies have revealed that the cytotoxicity of leukotoxin appears to result from the conversion of this epoxide to its corresponding vic-diol (9,10-DiHODE), a reaction catalyzed by epoxide hydrolase (Scheme 1). That is, it appears to be a metabolite (produced by epoxide The significance of this novel finding that epoxide hydrolase appears to bioactivate an inflammatory-derived mediator, and the clinical relevance of leukotoxin-mediated injuries, suggest the need for effective and site-specific inhibitors of epoxide hydrolase. Because at present there are few if any specific inhibitors of epoxide hydrolase that also do not affect other aspects of cellular homeostasis, another aspect of this invention is to use an assay system to evaluate classes of epoxide hydrolase inhibitors (e.g. chalcone oxides, glycidols, epoxy fatty acid esters) for effectiveness of inhibiting epoxide hydrolase which would have minimal side effects on cellular homeostasis.

Accordingly, another aspect of the present invention is a method of screening inhibitors of an epoxide hydrolase, comprising providing an insect cell system having insect cell growing therein. These insect cells are infected with a recombinant baculovirus that expresses epoxide hydrolase in the insect cells under cell growth conditions. A potential inhibitor of epoxide hydrolase is incubated with the insect cells of the insect cell system, and the insect cells are thereafter examined for viability. Activating enzymes which oxidize lipids to biologically active metabolites of precursors also are valuable. Particularly preferred are insect cells expressing reductase and P-450 as a single fusion.

In another aspect of the present invention, a method for assaying inhibitors of an epoxide hydrolase with reduced side effects in vivo comprises providing a cell system that includes a mammalian cell line where the cell line expresses an epoxide hydrolase and has a determinable level of intracellular free $Ca^{2+}$ or a determinable membrane permeability. The inhibitor candidate is incubated with the cell line and then the incubated cells are examined for a change in the intracellular free $Ca^{2+}$ or in membrane permeability. More preferably, the examining includes monitoring for a calcium influx.

In yet a further aspect of the present invention, antibody (polyclonal or monoclonal) are raised against DiHOxyEDEs, leukotoxin diols and other similar oxylipins and used for diagnostic or clinical applications.

A further aspect of this invention is the use of transgenic systems to produce leukotoxins, leukotoxin diols, DiHoxyEDEs, and other oxylipins using P450 and/or epoxide hydrolase. Among other uses these materials can be employed as drugs or prodrugs. For example low levels of leukotoxins are reported to have antimicrobial activity in animal and plant systems. We believe leukotoxin diol could be a selectable marker for recombinant plants and it could be used to control pathogens in plant systems. And, in yet a further aspect of this invention, novel DiHOxyEDEs are disclosed with biological activity.

Other objects and aspects of this invention will become apparent upon reading the following description and illustrative experimental data and results.

BRIEF DESCRIPTION OF THE DRAWINGS

The two parts of FIG. 1, panels (A) and (B), illustrate the effects of lipids on the bioelectric properties of primary cultured monolayers of rat pulmonary alveolar epithelial cells; and, The several parts of FIG. 2 graphically illustrate the effects of lipids on the viability of cultured cells of *Spodoptera frugiperda* that were infected with recombinant baculoviruses to produce various enzymes.

DETAILED DESCRIPTION OF THE PREFERRED EMBODIMENTS

Figure 1B:
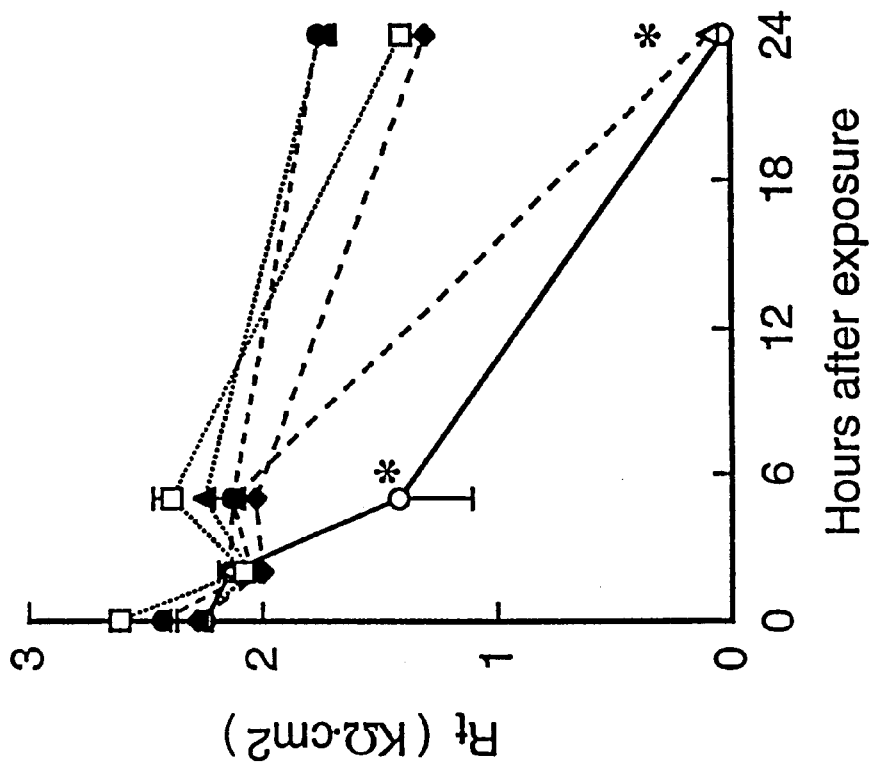

We here show by both in vitro and in vivo experiments that leukotoxin diols are much more toxic and cause much more pronounced symptoms at lower concentrations than do the parent leukotoxins. The leukotoxin diol concentrations showing biological activity in vitro are also consistent with in vivo levels of leukotoxin observed in burn and ARDS patients. These data indicate that the numerous pathologies attributed to leukotoxin and isoleukotoxin result from enzymatic activation mediated largely by the soluble epoxide hydrolase.

Our data with the enzymatic activation of leukotoxin and isoleukotoxin, both in vivo and in vitro, demonstrate the ability of the soluble epoxide hydrolase to metabolize a wide variety of oxylipins. By "oxylipin" is mean to refer to any fatty acid with additional oxygen—e.g. epoxides, diols, monohydroxys, prostagladins, and the like. These data indicate the conversion of arachidonic acid epoxides to diols and arachidonic acid diepoxides to tetrahydrofurandiols and tetraols. Thus, the present invention provides therapeutic methods based upon clinical intervention to prevent the pathways mediated by the epoxide hydrolase. In particular, practice of the present invention is directed to inhibiting the epoxide hydrolase by four classes of synthetic chemical enzyme inhibitors or by anti-sense nucleic acid.

Suitable epoxide hydrolase inhibitors are compounds providing alternate substrate for the enzyme, lipid alkoxides (e.g., the 9-methoxide of stearic acid), lipophilic diimides (e.g., dicyclohexylcarbodiimide), phenyl glycidols (e.g., SS-4-nithrophenylglycidol), and chalcone oxides.

Accordingly, a patient in need of therapy is administered an effective therapeutic amount of an epoxide hydrolase inhibitor or an anti-sense nucleic acid. Such administration will typically be in the form of a pharmaceutical composition where, for example, the inhibitor as active agent may be in an acid addition salt and the composition is formulated so as to be suitable-for oral or parenteral administration or as a suppository. Further, compositions suitable for injection constituted by aqueous injectable buffered or unbuffered isotonic and sterile saline or glucose solutions are contemplated. The active agent can also be used in compositions such as tablets or pills, preferably containing a unit dose, and may be mixed with conventional tabletting ingredients. Actual dosage levels of the epoxide hydrolase inhibitor can be varied to obtain the desired therapeutic response for a particular composition and method of administration. The total daily dose administered is contemplated to be from about 0.001 to about 100 μM/kg body weight. However, when practicing the invention a drug like clofibrate, which is known to induce the soluble epoxide hydrolase and cytochrome P-450, and a drug like acetaminophen, which depletes glutathione, should be avoided. This is because we have experimental data suggesting that when glutathione levels are depleted, then leukotoxin becomes more toxic. By contrast, parallel therapies designed to enhance alternate pathways of leukotoxin metabolism such as administration of N-acetylcysteine and glutathione and their methyl esters should be encouraged.

Other inhibitors of epoxide hydrolase and potential therapeutic agents for ARDS may be found by enzyme or cell based assays. In the former case, the putative inhibitor (such as those compounds based on steric and electronic properties of known substrates or through an understanding of enzyme mechanism) is added in a small volume (1 μl) of organic co-solvent to an aqueous solution of the recombinant or natural epoxide hydrolase. Following preincubation at 37° C. (0–10 minutes) substrate is added in 1 μl organic co-solvent and the sample incubated for 1–10 minutes. The diol is monitored spectrophotometrically (Wixtrom et al., *Analy. Biochem.*, 174, pp. 291–299, 1988; Dietz et al.,*Analy. Biochem.*, 216, pp. 176–187, 1994), or radiochemically (Borhan et al., *Analy. Biochem.*, 231, pp. 18–200, 1995).

For cell based assays linoleate or leukotoxin may be added in organic co-solvent followed by a putative inhibitor to insect cells infected or transfected with a recombinant baculovirus. For example, Sf cells transfected with P-450, epoxide hydrolase, glutathione transferase, or other relevant genes may be prepared as recently described by several of us (See Grant et al., *Biochem. Pharmacol.*, 51, pp. 503–515, 1996). Cell viability may be read with MTT.

Among the epoxide hydrolase inhibitors that may be used in practicing this invention are alternative substrates for the enzyme, such as the epoxide of methyl oleate and other fatty acids and esters or methyl epoxyoctadecenoate (EpOD) administered i.v. into the femoral vein or aspirated into the lung. Also, as earlier noted, chalcone oxides and phenyl glycidols are epoxide hydrolase inhibitors. Among suitable chalcone oxides for this use are those illustrated by Table A.

TABLE A
| structure inhibitors: | n° | Mouse sEH IC50 (μM) | Human sEH IC50 (μM) |
|---|---|---|---|
| 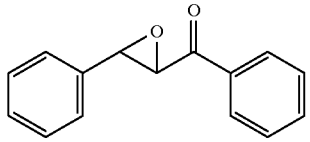 | 1 | 2.9 ± 0.3 | 0.3 ± 0.1 |
| 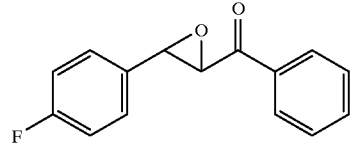 | 2 | 1.3 ± 0.3 | 0.3 ± 0.1 |
| 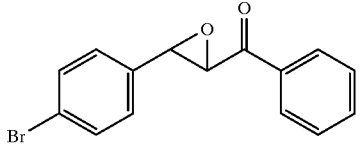 | 3 | 0.7 ± 0.1 | 0.20 ± 0.05 |
| 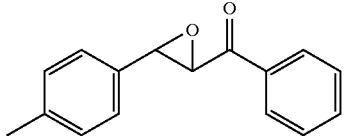 | 4 | 1.9 ± 0.2 | 0.36 ± 0.04 |
| 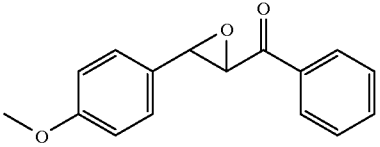 | 5 | 0.20 ± 0.02 | 0.11 ± 0.01 |
| 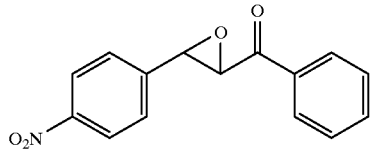 | 6 | 1.8 ± 0.3 | 0.63 ± 0.01 |
| 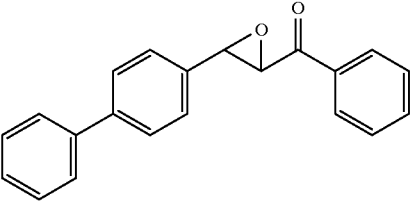 | 7 | 0.14 ± 0.01 | 0.20 ± 0.01 |
| 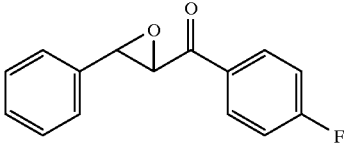 | 8 | 1.8 ± 0.2 | 0.39 ± 0.09 |

TABLE A-continued

| structure inhibitors: | n° | Mouse sEH IC50 ($\mu$M) | Human sEH IC50 ($\mu$M) |
|---|---|---|---|
| 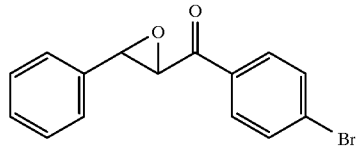 | 9 | 0.6 ± 0.1 | 0.22 ± 0.01 |
| 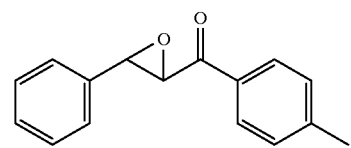 | 10 | 1.7 ± 0.2 | 0.23 ± 0.02 |
| 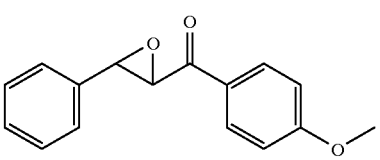 | 11 | 0.32 ± 0.04 | 0.20 ± 0.04 |
| 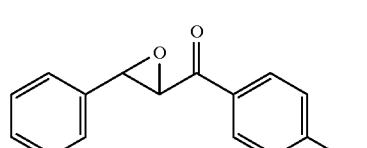 | 12 | 1.5 ± 0.2 | 0.25 ± 0.01 |
| 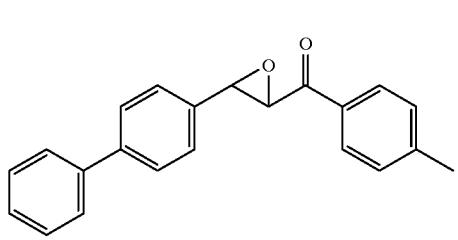 | 13 | 0.10 ± 0.01 | 0.19 ± 0.03 |
| 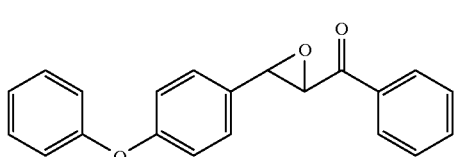 | 14 | 0.14 ± 0.02 | 0.51 ± 0.03 |
| 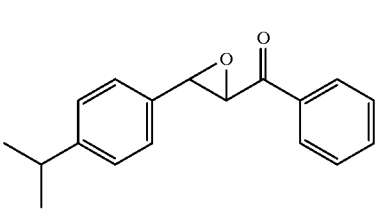 | 15 | 0.47 ± 0.01 | 0.48 ± 0.01 | values are means of 3 experiments.

As shown by the data of Table A, tests in both mouse and human enzymes were conducted for inhibition of soluble epoxide hydrolase, with the IC50 values being given wherein the mouse sEH values were conducted at 8 $\mu$g/ml (0.3 $\mu$M) and the human sEH at 16 $\mu$g/ml (0.26 $\mu$M).

Among suitable chalcone oxides are included 4-phenylchalcone oxide and 4-fluourochalcone oxide. Suitable glycidols include S,S-4-nitrophenylglycidol. These are believed to form stable acyl enzymes and transition state mimics. Alternatively, alkoxylipids or hydrocarbons have been shown to be competitive inhibitors. The alkoxy group ($OCH_3$, $OC_2H_5$, $OC_3H_9$) are believed to be hydrolytically stable steric mimics of the substrate. The general structure is $RCH(OCH_3)R'$ for a methoxide where R and R' are hydrophobic. A typical compound is 9-methoxyoctadecanoic acid. They can be prepared in high yield from the corresponding olefin by Brown oxymercuration-demercuration in the appropriate solvent (for example, ethanol for ethoxides and methanol for methoxides).

However, because these specific inhibitors can affect other aspects of cellular homeostasis, a continued search for other therapeutically effective epoxide hydrolases inhibitors with minimal side effects is desirable. This search is facilitated by practice of other aspects of the invention wherein means for screening potentially useful epoxide hydrolase inhibitors and for assaying side effects are provided as follows.

A simultaneous incubation of leukotoxin or isoleukotoxin and the potential inhibitor may be performed with insect cells, such as, for example, Sf-21 cells, expressing soluble epoxide hydrolase. After sufficient incubation, for example 2–5 hours, these protect Sf-21 cells expressing that enzyme. Among the advantages of such a system over enzyme assays is that bioactivity of potential inhibitors (through cellular membrane) is already taken into account, so that inhibitors with a high degree of toxicity to cells will be excluded from further scrutiny and there will be no radioactive waste. This assay will be further described hereinafter.

Among the aspects of this invention are discoveries involving an arachidonic acid (AA) pathway. AA can be metabolized by cytochrome p-450 epoxygenase to yield epoxyeicosatrienoic acids (EETs). These EETs can be further metabolized by soluble epoxide hydrolase to yield the corresponding dihydroxyeicosatrienoic acids (DHETs). Studies have shown that the EETs and DHETs have a whole host of biological activities such as inhibition of Na/K ATPase, vasodilation of coronary artery, and mobilization of $Ca^{2+}$ and inhibition of platelet aggregation. Similarly, cytochrome P-450 epoxygenase converts free linoleic acid to 9,10-epoxy-octadec-12-enoate (leukotoxin).

Another aspect of the present invention is our finding that cytochrome P-450 epoxygenase can also convert free fatty acids, including AA, to various positional diepoxides as well as monoepoxides (EETs), and these diepoxides of AA (diepoxyeicosadienoates or DiEpEDE) are in turn metabolized by soluble epoxide hydroxylase into previously unknown DiHOxyEDEs. We have synthesized and purified 5 membered cis- and 5 trans-regio- and positional isomers of DiHOxyEDEs and found some of them to be biologically active, which novel compounds are illustrated in Table 1.

We have been able to detect biosynthesis for these biologically active DiHOxyEDEs in biological matrices. This discovery serves to further extend the P-450/epoxide hydrolase branch of an AA pathway, and we believe it may have direct implications for treating ARDS. Further, we believe this third AA pathway is involved in a variety of other cell mediated events, including diabetes.

Many signal transduction pathways involve the arachidonic acid cascade. This cascade is initiated when a specific ligand such as a hormone or growth factor binds to its cell surface receptor, which in turn activates a phospholipase. Phospholipase $A_2$ cleaves the fatty acid in the second acyl position from phospholipids in the inner leaflet of the plasma membrane. Arachidonic acid is commonly found in this position. The free arachidonic acid is metabolized into a myriad of important regulatory molecules involved in such events as cell activation, cell division, chemotaxis, inflammation, ovulation, and wound healing. There are two well studied pathways of arachidonic acid metabolism. The first is the cyclooxygenase pathway which leads to the production of prostaglandins and eventually to thromboxanes and prostacyclins. The second is the lipoxygenase pathway which converts arachidonic acid to compounds such as a variety of leukotrienes. The products of the arachidonic acid (AA) cascade can be released by the cells and then bind to specific cell surface receptors on other types of cells. The receptors for leukotrienes, thromboxanes, and prostaglandins are often coupled to the phosphatidylinositol pathway, which causes a rise in intracellular free $Ca^{2+}$. Initially the rise from intracellular free $Ca^{2+}$ is due to the release from endoplasmic reticulum. This rise in intracellular $Ca^{2+}$ in turn leads to the production of an unidentified second messenger that stimulates $Ca^{2+}$ influx from the extracellular space. Therefore assays for the potency of AA metabolites often involve their ability to cause a rise in intracellular $Ca^{2+}$. As will be seen, an aspect of this invention is the discovery of novel arachidonic acid metabolites that we show to have biological activity and wherein assays in accordance with the invention can be performed to determine whether and an extent that intracellular $Ca^{2+}$ is affected.

We view an important therapeutic application for an aspect of this invention to be in treating diseases of the lung. The lung, with its extensive surface area exposed directly to the environment, is particularly susceptible to oxidant injury and products of inflammation. Since the entire cardiac output passes through the pulmonary artery, the lungs can also be injured by blood-borne agents. The cellular heterogeneity of mammalian lung complicates direct study of those pulmonary cells most susceptible to injury. Furthermore, the complex pulmonary anatomy renders it difficult to distinguish precisely where biological agents are metabolized in lung tissues. The target tissue and sequence of events underlying alveolar edema are not conclusively established; consequently, the interrelationships and relative contributions of endothelial versus epithelial versus inflammatory compartments in mitigating damage to the air-blood barrier remain equivocal.

Since alveolar epithelium provides the principal resistance to the flow of fluid and solutes across the air-blood barrier, our experimental methodologies have focused on this component, using an established in vitro physiological model of the alveolar epithelial barrier. The use of the serum-free culture system, along with synthesized and purified oxylipins, permits mechanistic experiments designed to elucidate the cellular processes critical in the maintenance and resolution of alveolar epithelial barrier function.

The ARDS ailments are seen in a variety of patients with severe burns or sepsis. Sepsis in turn is one of the SIRS syndromes. In ARDS there is an acute inflammatory reaction with high numbers of neutrophils that migrate into the interstitium and alveoli. If this progresses there is increased inflammation, edema, cell proliferation, and the end result is impaired ability to extract oxygen. ARDS is thus a common complication in a wide variety of diseases and trauma. The only treatment is supportive. There are an estimated 150,000 cases per year and mortality ranges from 10% to 90%.

The exact cause of ARDS is not known. However it has hypothesized that over-activation of neutrophils leads to the release of linoleic acid in high levels via phospholipase $A_2$ activity. Linoleic acid in turn is converted to 9,10-epoxy-12-octadecenoate enzymatically by neutrophil cytochrome P-450 epoxygenase. This lipid epoxide, or leukotoxin, is found in high levels in burned skin and in the serum of burn patients. Furthermore when injected into rats, mice, dogs, and other mammals it causes ARDS. The mechanism of action is not known.

Just as the epoxide products of AA (DiEpEDEs) can be metabolized by soluble epoxide hydrolase to produce the DiHOxyEDEs, the linoleate epoxide (leukotoxin) can also be converted by soluble epoxide hydrolase 9,10-DiHODE.

This leukotoxin-diol is analogous to the DiHOxyEDEs. The leukotoxin does not cause a rise in intracellular $Ca^{2+}$ in alveolar cells. However the 9,10-DiHODE does cause a dramatic rise in intracellular $Ca^{2+}$. We believe that much of the damage to the alveolar cells in ARDS may be triggered by an enormous rise in intracellular free $Ca^{2+}$. The rise in intracellular $Ca^{2+}$ is believed to be caused by both the 9,10-DiHODE and 12,13-DiHODE. Cell damage and cell death in general are often caused by an irreversible rise in intracellular $Ca^{2+}$. Thus, for the first time a mechanism for ARDS may be proposed.

Polyunsaturated lipids such as linoleic and arachidonic acid serve as precursors of biologically active metabolites. The addition of a single oxygen atom, via chemical or enzymatic processes, to an olefin or hydrocarbon of these essential fatty acids produces epoxides and other oxygen containing metabolites (collectively referred to as oxylipins) that are key intermediates in biosynthetic pathways. For example, a 5-lipoxygenase metabolite of arachidonic acid (e.g., leukotriene $A_4$) exhibits direct biological activity and is metabolized to potent mediators. A P-450 monooxygenase metabolite of arachidonate, 5,6-epoxyeicosatrienoate, has been hypothesized to be a second messenger for agonist-induced cell calcium entry. One pathway for elimination of these compounds involves hydration by epoxide hydrolases. These enzymes, which convert epoxides to putatively less reactive (and more water soluble) diols, are found in all vertebrate tissues, with highest levels expressed in the liver and kidney. The role of epoxide hydrolases, which are thought to provide cellular protection from exogenous and endogenous epoxides has been considered to be one of detoxification.

Epoxide hydrolase (EH) is a ubiquitous enzyme found in all vertebrate tissues tested with maximum concentrations found in the liver and kidney. There are two main types of EH with broad substrate specificity, microsomal epoxide hydrolase (MEH), and soluble epoxide hydrolase (SEH). Both enzymes are members of the $\alpha/\beta$-hydrolase fold family. Unlike cholesterol epoxide hydrolase and leukotrine $A_4$ hydrolase, they convert epoxides to diols by a two step mechanism involving an isolatable, covalent acyl enzyme intermediate. Both enzymes metabolize epoxides to trans-diols or trans-vicinal diols. Compounds hydrolyzed by EH are more hydrophilic and hence more easily excreted than the parent compound. Thus EH is usually thought of as a pathway towards detoxification. However, occasionally EH activates a compound to a highly reactive and more toxic species, such as in the case of benzo(a)pyrene. A convenient method for monitoring the products formed by EH is to add the substrate directly to the purified enzyme. However, this does not provide any information about metabolism product toxicity or the behavior of the substrate and/or the metabolite in a cellular environment.

We first observed that neither leukotoxin nor isoleukotoxin induced cytotoxicity in an insect cell line (Sf-21 cells) that normally expresses very low levels of endogenous epoxide hydrolase activity; however, the corresponding diols did. Using a baculovirus expression system in this model, we established that leukotoxin was cytotoxic only to cells in which epoxide hydrolase had been transfected, confirming the role of this enzyme in the bioactivation of leukotoxin. We subsequently examined the selective toxicity of leukotoxin-derived oxylipins in our mammalian lung model (i.e., monolayers of primary cultured rat alveolar epithelial cells).

As earlier briefly noted, we have developed a screening method whereby baculoviruses expressing cloned murine and human SEH are transfected into insect cells, such as into Spondoptera frugiperda insect cells (Sf-21 cells). A description of these transfected insect cells has recently been published. See, Grant et al., "Development of an in situ Toxicity Assay System Using Recombinant Baculoviruses," Biochem. Pharmacol., 51, pp. 503–515, 1996, which is incorporated in its entirety by reference. The significant advantage this insect cell system has over other cell systems is its relatively high levels of transgenic enzyme and very low levels of endogenous enzymes. Therefore interferences from endogenous enzymes as found on other cell culture systems is not a problem.

However, there remains an advantage of using mammalian cell cultures to test toxicity, since the environment in a mammalian cell is closer to the physiological environment of a human cell than that of the Sf-21 cell system. Hence, another cell system involving primary monolayer of rat alveolar type II cells has been developed to test cytotoxicity. In this system, cells are monitored for injuries such as membrane permeability and calcium influx. The assay system may be prepared as follows.

Pulmonary alveolar epithelial cells are isolated from adult rats using procedures reported previously. (Cheek et al., Toxicol. Appl. Pharmacol., 125, pp. 59–69, 1994). Briefly, rats are anesthetized, tracheostomized, and exsanguinated. Following perfusion of the pulmonary vasculature, excised lungs are filled with an emulsion of Fluorinert FC-75 (3M, St. Paul, Minn.) and bovine serum albumin in balanced salt solution for 20 minutes at 37° C. After displacement of the emulsion by lavage, a solution of elastase is infused via the airways and allowed to incubate for 20 minutes at 37° C. Elastase-digested lungs are minced, filtered, and pooled to yield a single cell suspension which is then centrifuged on a discontinuous Percoll gradient. The resulting enriched cell suspension is further purified using the IgG panning method (Dobbs et al., Am. Rev. Resp. Dis., 134, pp. 141–145, 1986) to yield a final cell suspension of ~80% type II alveolar epithelial cells. For physiological studies, isolated type II cells are plated onto tissue culture-treated Transwell inserts (Costar, Van Nuys, Calif.) in Ham's F-12 supplemented with 10% newborn bovine serum and 0.1 $\mu$M dexamethasone (Sigma, St. Louis, Mo.) at a seeding density of $1.5 \times 10^6$ cells/cm². For imaging experiments (e.g., calcium influx studies), isolated type II cells are plated onto glass coverslips. After 48 hours in culture at 37° C. in 5% $CO_2$/air, the initial medium is removed from the cultures and replaced with serum-free F-12+6 nutrient medium consisting of Ham's F-12 supplemented with sodium bicarbonate (14 mM), N-2-hydroxyethylpiperazine-N'-2-ethanesulfonic acid (HEPES, 10 mM) and L-cystine (0.15 mM) and containing the following growth factors: insulin (5 $\mu$g/ml), transferrin (5 $\mu$g/ml), epidermal growth factor 25 ng/ml), hydrocortisone (1 $\mu$M), bovine hypothalamus extract (7.5 $\mu$g/ml) and retinol (0.1 $\mu$M) as previously described (Cheek et al., ibid). Monolayers are then incubated in serum-free medium for an additional 24–48 hours and then removed from the incubator for cytotoxicity studies.

In both cell systems noted above, cytotoxicity studies were performed on the methyl esters and free acids of linoleic acid, leukotoxin, isoleukotoxin, leukotoxin vic-diol, and isoleukotoxin vic-diol. Although previous researchers have suggested that leukotoxin was the compound eliciting toxic responses in burn patients, the results from the Sf-21 cells expressing Lac Z and the rat alveolar type II cells showed no cytotoxic signs after exposure to methyl linoleate, methyl leukotoxin, nor methyl isoleukotoxin. Additionally, not only did both vic-diols prove to be highly toxic in both systems but also, cell death occurred in Sf-21 cells expressing EH exposed to methyl leukotoxin and methyl isoleukotoxin. Therefore, data suggest that it is the diol resulting from EH activity, not the epoxide, that is causing toxicity associated with burn victims and possibly ARDS patients.

Our preliminary studies in mouse liver had led us to the discovery of the tetrahydrofuran-diols of arachidonic acid. Methyl esters of these compounds caused in vitro activation of human polymorphonuclear leukocytes, while in the same assays their progenitor methyl diepoxyarachidonates were not bioactive. Exhibition of such differential biological effect implied an activation of the diepoxides by soluble epoxide hydrolases and suggested a proinflammatory role for the tetrahydrofuran-diols of arachidonic acid.

In other experiments, a set of methyl arachidonate analogs, methyl arachidonate methoxides, displayed inhibitory effects toward purified soluble epoxide hydrolase (sEH). The importance of this finding was that the compounds potentially could serve as biochemical tools in the studies designed to determine the roles of sEH in vivo. In addition, should the products of sEH be unequivocally implicated in the development of inflammation, such inhibitors may serve as pharmaceutical agents in prevention of inflammatory ailments. Another type of biological activity associated with the methyl arachidonate methoxides is their in vitro growth inhibition of and cytotoxicity towards keratinocytes at certain concentrations. Finally, these compounds seem to be biologically active in plants and they were able to induce phytoalexin production in potato tubers infected with a pathogenic fungus.

Synthesis of methyl arachidonate THF-diols resulted from epoxidation of methyl arachidonate followed by separation of its diepoxides and acidic hydrolysis and cyclization—the acid catalyses both the hydrolysis and cyclization processes of these diepoxides. The hydrolysis products then underwent column chromatography to separate the methyl arachidonate THF-diols from the rest of the mixture. These synthetic THF-diols were used as standards in the negative ion chemical ionization gas chromatography mass spectroscopy method which led us to the discovery of these compounds as natural products in mouse liver. In addition, these synthetic compounds were used in in vitro polymorphonuclear leukocyte activation assays. Activation of these leukocytes were determined using an established flowcytometric method.

Methyl arachidonate methoxides were produced by methoxymercuration of methyl arachidonate which led to a net addition of MeOH to one or more double bonds and resulted in a mixture of mono-, di-, tri, and tetramethoxy arachidonates. After separation of the unreacted methyl arachidonate from the rest of the mixture, the methoxide mixture of methyl arachidonate was determined to be an inhibitor of soluble epoxide hydrolase using a standard TSO inhibition assay. The inhibitory levels of this mixture of compounds were 98% at 100 $\mu$M, 95% at 10 $\mu$M, and 30% at 1 $\mu$M. Because of this important finding we became interested in the general toxicity of these compounds and decided to test their toxicity by incubating them with keratinocytes in vitro and measuring their cytotoxicity to or growth inhibition of these cells. At about 100 $\mu$M levels, these compounds proved 100% cytotoxic to the cured keratinocytes. In another experiment, at about 10 $\mu$M levels these compounds completely inhibited the growth of the aforementioned cells. It was also discovered that methyl arachidonate methoxides were able to induce phytoalexin production in potato tubers infected by a fungus when applied at 50 $\mu$g/disk. Phytoalexin production is important in disease fighting capabilities of plants when infected by pathogens.

Methyl leukotoxin and methyl isoleukotoxin, and their diols were chemically synthesized from methyl linoleate using m-chloroperbenzoic acid, as described previously and illustrated by Scheme 1. These two monoepoxides and the diastereomers of the 9,10-12,13-diepoxide (not shown) were separated from each other and interfering compounds using normal-phase silica column chromatography. Each of these monoepoxides then were hydrolyzed to its diol using perchloric acid and purified or enzymatically with recombinant soluble epoxide hydrolase. The purity and identity of all compounds were confirmed using a combination of at least thin layer chromatography (TLC), gas chromatography (GC), gas chromatography low resolution electron impact mass spectrometry (GC/LRNI/MS), and $^1$H and $^{13}$C. nuclear magnetic resonance (NMR) and comparisons of these data to those found in the literature. Free fatty acids were purified using the same solvent system containing 1% acetic acid. The toxicity of the compounds were evaluated in Sprague-Dawley rats from Simonson Laboratories, Gilroy, Calif.

Rats received free fatty acids dissolved in phosphate buffered saline containing 5% DMSO by cardiac puncture after they were anesthetized by intraperitoneal injections of pentobarbital. Exposure of the pulmonary system to pure leukotoxin diol caused immediate respiratory distress with death in less than 2 hours when 35 mg/kg were injected. No clear symptoms or mortality were observed with doses of the parent leukotoxin up to 100 mg/kg. Male Swiss-Webster mice (18–20 g) from Bantin-Kingman (Fremont, Calif.) received tail vein injections of free fatty acids dissolved in 2-methoxyethanol after they were anesthetized by inhaling methoxyfluorane. When 200 mg/kg of a mixture of leukotoxin/isoleukotoxin diol was administered, 30% mortality occurred within 4 minutes. All of the mice treated were lethargic and exhibited difficulty breathing for at least 2 hours. In contrast, no toxicity was observed with the parent leukotoxins at 200 mg/kg. At 500 mg/kg of the leukotoxins only 25% mortality was observed with death between 18 and 24 hours, and in no animal were symptoms observed for more than 10 minutes. No lethal effects or symptoms were observed following intraperitoneal or subcutaneous injections of leukotoxin, isoleukotoxin, or their diols at doses up to 175 mg/kg.

Sf-21 cells were infected with recombinant baculoviruses producing either human soluble epoxide hydrolase (hsEH), mouse soluble epoxide hydrolase (msEH), human microsomal epoxide hydrolase (hmEH), or β-galactosidase (Lac Z) as a control virus. Two days post-infection varying concentrations of lipids were added dissolved in 2% final concentration of DMSO (v/v). Three days post-infection a viability test was performed with MTT (3-[4,5-dimethylthiazol-2-yl]-2,5-diphenyl-tetrazolium bromide).

Turning to FIG. 2(A), methyl linoleate produced no change in viability. In FIG. 2(B), methyl leukotoxin was not toxic to Lac Z expressing cells, mildly toxic to hmEH expressing cells but was toxic ($LC_{50}$~290 $\mu$M) to cells expressing either human or mouse sEH. In FIG. 2(C), methyl leukotoxin diol was toxic ($LC_{50}$~160 $\mu$M) to all cell types. In FIG. 2(D), methyl isoleukotoxin was not toxic to Lac Z expressing cells, mildly toxic to hmEH expressing cells, and toxic ($LC_{50}$~150 $\mu$M) to those cells expressing mouse or human sEH. In FIG. 2(E), methyl isoleukotoxin diol was toxic ($LC_{50}$~200 $\mu$M) to all cells showing that the hydrolysis of the epoxides of methyl leukotoxin and methyl isoleukotoxin to their diols causes the toxicity attributed to these compounds.

All experiments were replicated 3 to 7 times on different days. All of the replicates were used in the calculation of $LC_{50}$'s with the upper and lower fiducial limits calculated with the program Polo. Results similar to the ones reported here for methyl esters were obtained with free fatty acids (data not shown). The diepoxides were much less toxic ($LC_{50}$~600 $\mu$M) and their hydration products (data not shown) caused no toxicity to any cell type at concentrations up to 1 mM.

The following data in FIG. 1 are presented as mean±standard deviation; n=5–10 monolayers. (*) indicates mean significantly less than that of the parent lipid (methyl linoleate) at the same time after exposure as determined by one way ANOVA/Scheffe contrast.

Figure 1A:
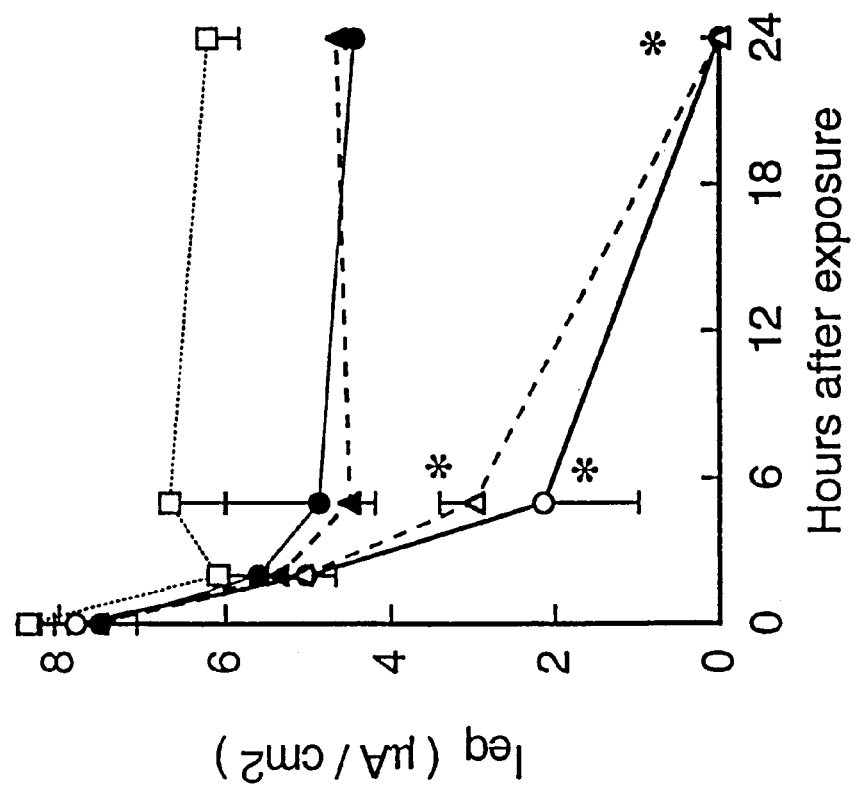

With reference to FIG. 1, monolayers were treated with 300 $\mu$M methyl linoleate (open squares, dotted line), methyl leukotoxin (black triangles, dashed lines), methyl isoleukotoxin (Black circles, solid lines), methyl leukotoxin diol (open triangles, dashed lines), or methyl isoleukotoxin diol (open circles, solid lines), delivered in less than 2% methanol (v/v). Immediately prior to exposure (0 hour) and at various times after administration of lipid, monolayer bioelectric properties [transepithelial resistance ($R_t$), short-circuit current ($I_{eq}$)] were recorded using a voltohmmeter as previously described. In FIG. 1(A), treatment of monolayers with 300 $\mu$M leukotoxin diol or isoleukotoxin diol resulted in decreased $I_{eq}$ by five hours following exposure, indicative of reduced net transepithelial ion transport. Complete absence of $I_{eq}$ 24 hours following exposure suggested loss of epithelial cell viability. In FIG. 1(B), $R_t$ values of same monolayers shown in (A). Decreased $R_t$ was noted at five hours following exposure to 300 $\mu$M isoleukotoxin, indicating that paracellular permeability increased as a result of lipid administration. By 24 hours after exposure to either methyl leukotoxin diol or methyl isoleukotoxin diol, $R_t$ values were negligible, confirming a decrease in cell viability and monolayer integrity as a result of treatment with either diol. No biological activity was observed in this system with the parent compound, monoepoxide(s), or diol (s) in the methyl oleate series. In separate experiments only methyl leukotoxin diol and methyl isoleukotoxin diol were effective at increasing intracellular calcium monitored by Fura-2 with 50 $\mu$M the lowest effective dose in alveolar epithelial cells while the other compounds were inactive at doses up to 300 $\mu$M (data not shown).

Further, we performed an in vitro enzymatic hydrolysis of AA methylene-interrupted diepoxides of diepoxyeicosadienoates (DiEpEDEs) to their THF-diols or dihydroxy-oxyeicosadienoates (DiHOxyEDEs) and tested these for biological activity.

Thus, methyl DiEpEDE and DiHOxyEDE standards were prepared and their structures were confirmed. The identity of DiHOxyEDE standard mixtures were defined using gas chromatography negative ion chemical ionization mass spectrometry, that is gas/liquid chromatography interfaced with negative chemical ionization mass spectrometry (GC/NICI/MS), after its conversion to pentafluorobenzyl (PFB) ester trimethylsilyl (TMS) ethers using standard methodology. The rationale for not employing a diastereomerically pure standard was to encompass all diastereomers potentially present in vivo. The GC/NICI/MS analysis of these derivatized compounds yielded a very clear diagnostic fragment at m/z 497 which represented all possible diastereomers of bis-TMS ether carboxylate anions ([M-PFB]$^-$) of DiHOxyEDE. Furthermore, DiHOxyEDE PFB ester bis-d$^9$-TMS ethers yielded m/z at 515; confirming presence of only two hydroxyl groups. Hydrogenated PFB ester bis-TMS ethers yielded a m/z 501; indicating presence of two olefins. Unfortunately, such detection methods could not be applied to DiEpEDEs because these compounds seemed to undergo rearrangements, thereby hindering detection of the corresponding carboxylate anion.

In order to investigate biogenesis of DiEpEDEs, livers from clofibrate-fed mice were extracted, saponified, and derivatized. Analysis of the PFB ester TMS ether derivatives of extracts from clofibrate-fed mouse livers revealed presence of compounds which yielded m/z 497 at the same retention time as our authenticated mixtures of standards. Furthermore, enrichment of liver samples with the synthesized standard mixture led to coelution of the analytes with the standards. Additionally, the analytes in the processed lipid extracts behaved identical to our synthetic standards under all other derivatization conditions described above. Treatment of methyl arachidonate with our extraction, hydrolysis, and derivatization procedures did not yield DiHOxyEDEs. This ruled out the possibility of artifactual production of DiEpEDEs and DiHOxyEDEs from AA. While elimination of the hydrolysis step from our methodology eliminated DiHOxyEDE production from synthetic DiEpEDE standards (free acid), it did not entirely inhibit detection of DiHOxyEDEs in liver extracts. This established DiHOxyEDEs as authentic metabolites of AA in mouse liver. Furthermore, because we were able to form DiHOxyEDE PFB esters without hydrolysis of lipid extracts, one may conclude that DiHOxyEDEs existed in the cells in their free acid forms.

Elevated DiHOxyEDE concentrations in our saponified preparations indicates that, in the absence of a hydrolysis step, a fraction of detected DiHOxyEDEs were formed via hydrolysis of epoxides in DiEpEDEs and/or acylated DiEpEDEs and DiHOxyEDEs. Conversely, the increased levels of DiHOxyEDEs in clofibrate-treated mice tissues suggests a biological rather than an auto-oxidative pathway for their production. Another possibility is that an increased concentration of $H_2O_2$ resulting from proxisome proliferation is responsible for some of AA epoxidation which in turn leads in DiHOxyEDE production. The significance of this route of epoxidation may be minimal because inducibility of cytochrome P-450s by clofibrate has been established. Finally, tissues from obese Zucker rats contain higher levels of DiHOxyEDEs than those of the lean animals. Because obese Zucker rats are prone to diabetes, this may suggest a physiological role of DiHOxyEDEs in etiology of that ailment.

In an effort to define the biological activity of DiEpEDEs and DiHOxyEDEs, these compounds were prepared chemically and separated as their methyl esters. Next, methyl AA, diastereomeric and positional mixtures of methyl DiEpEDEs, and methyl DiHOxyEDEs were tested in a calcium influx assay employing isolated rat pulmonary alveolar epithelial cells.

Methyl DiHOxyEDE mixture caused an immediate, fast, and sustained rise in influx of $Ca^{2+}$ from the media into the cells (data not shown). Furthermore, DiHOxyEDEs have proved to be non-toxic to keratinocytes and fibroblasts over a long period of time. Upon exposure to methyl DiEpEDE mixture there was a delayed, slow, and transient rise in $Ca^2$+influx in the epithelial cells. The limited extent of activity observed by the diepoxides may have been caused by their in situ conversion to DiHOxyEDEs. Methyl AA did not affect influx of $Ca^{2+}$ into the pulmonary epithelial cells even though these cells were responsive to a $Ca^{2+}$ ionophore.

In order to study the quantitative structure/activity relationship of methyl DiHOxyEDEs, they were further purified and incubated individually with pulmonary epithelial cells. As can be observed, all the compounds which were trans across the tetrahydrofuran ring (hereinafter referred to as trans isomers) were virtually inactive in causing an influx of $Ca^{2+}$. Invariably, regioisomers with exocyclic hydroxyl group on the ω-terminus of the fatty acid were more potent.

In addition, mid-chain oxidation augmented the potency of DiHOxyEDEs.

Table 1 illustrates novel, biologically active compounds that we have discovered together with some activity data.

TABLE 1

| Structure | No. | % Increase in intracellular calcium 5 min. post-exposure | 10 min. post-exposure |
|---|---|---|---|
| cis-DiHOxyEDEs Structures | | | |
| [structure] | 1 | 48 ± 47 | 70 ± 71 |
| [structure] | 2 | DATA NOT AVAILABLE | |
| [structure] | 3 | 161 ± 48 | 201 ± 30 |
| [structure] | 4 | 28 ± 7 | 24 ± 7 |
| [structure] | 5 | 143 ± 33 | 90 ± 48 |
| [structure] | 6 | 23 ± 13 | 11 ± 7 |
| trans-DiHOxyEDEs Structures | | | |
| [structure] | 7 | 11 ± 4 | 16 ± 4 |

TABLE 1-continued

| No. | % Increase in intracellular calcium 5 min. post-exposure | 10 min. post-exposure |
|---|---|---|
| 8 | DATA NOT AVAILABLE | |
| 9 | 4 ± 6 | 6 ± 6 |
| 10 | 2 ± 7 | 3 ± 7 |
| 11 | −2 ± 8 | −4 ± 7 |
| 12 | 0 ± 6 | −5 ± 3 |

TABLE 2

| Table 1 No. | IUPAC | Trivial |
|---|---|---|
| 1 | Methyl cis-6,9-dihydroxy-5(8)-oxy-11(Z),14(Z)-eicosadienoate | Methyl cis-Iω DiHOxyEDE |
| 2 | Methyl cis-5,8-dihydroxy-6(9)-oxy-11(Z),14(Z)-eicosadienoate | Methyl cis-IΔ DiHOxyEDE |
| 3 | Methyl cis-9,12-dihydroxy-8(11)-oxy-5(Z),14(Z)-eicosadienoate | Methyl cis-IIω DiHOxyEDE |
| 4 | Methyl cis-8,11-dihydroxy-9(12)-oxy-5(Z),14(Z)-eicosadienoate | Methyl cis-IIΔ DiHOxyEDE |
| 5 | Methyl cis-12,15-dihydroxy-11(14)-oxy-5(Z),8(Z)-eicosadienoate | Methyl cis-IIIω DiHOxyEDE |
| 6 | Methyl cis-11,14-dihydroxy-12(15)-oxy-5(Z),8(Z)-eicosadienoate | Methyl cis-IIIΔ DiHOxyEDE |
| 7 | Methyl trans-6,9-dihydroxy-5(8)-oxy-11(Z),14(Z)-eicosadienoate | Methyl trans-Iω DiHOxyEDE |
| 8 | Methyl trans-5,8-dihydroxy-6(9)-oxy-11(Z),14(Z)-eicosadienoate | Methyl trans-IΔ DiHOxyEDE |
| 9 | Methyl trans-9,12-dihydroxy-8(11)-oxy-5(Z),14(Z)-eicosadienoate | Methyl trans-IIω DiHOxyEDE |
| 10 | Methyl trans-8,11-dihydroxy-9(12)-oxy-5(Z),14(Z)-eicosadienoate | Methyl trans-IIΔ DiHOxyEDE |
| 11 | Methyl trans-12,15-dihydroxy-11(14)-oxy-5(Z),8(Z)-eicosadienoate | Methyl trans-IIIω DiHOxyEDE |
| 12 | Methyl trans-11,14-dihydroxy-12(15)-oxy-5(Z),8(Z)-eicosadienoate | Methyl trans-IIIΔ DiHOxyEDE |

As summarized by Tables 1 and 2, the novel compounds of this third AA cascade, namely DiEpEDEs and the 5 trans and the 5 cis isomers of DiHOxyEDEs, were tested for their ability to cause a rise in intracellular free $Ca^{2+}$ in rat pulmonary alveolar cells. First we tested the effect of the parent molecule methyl AA and found it had no ability to trigger a rise in intracellular $Ca^{2+}$. Interestingly, incubation of these cells with methyl DiHOxyEDEs for more than 24 hours did not result in cell death. Next we tested a mixture of the diastereomeric and positional isomers of DiEpEDEs and found that at concentrations ranges from 20 $\mu$M to 300 $\mu$M it caused a gradual but persistent rise in intracellular $Ca^{2+}$ in a dose dependent manner. DiEpEDEs are converted to DiHOxyEDEs, therefore their gradual effect may be due to its slow conversion to DiHOxyEDEs by cellular epoxide hydrolases. A racemic mixture of the cis and trans regioisomers of DiHOxyEDEs caused a dramatic and immediate rise in intracellular $Ca^{2+}$.

As summarized in Table 1, the intracellular calcium measurement was performed as follows. Intracellular free $Ca^{2+}$ was measured using the fura-2 method (Grynkiewicz et al, *J. Biol. Chem.*, 260, pp. 3440–3450, 1985). Cells grown on coverslips were loaded with fura-2/AM (1 $\mu$M) (Molecular Probes Inc., Eugene, Oreg.) for 20 minutes at 37° C. The cells were then rinsed from physiological buffer and mounted on an inverted microscope that was attached to a spectrofluorimeter (Photon Technology Inc.). Individual cells were excited alternately at 340 nm and 380 nm and emission was measured at 510 nm for both excitation wavelengths. The fluorscence ratio (340/380) is an indirect measurement of intracellular free $Ca^{2+}$. For measurements of influx of extracellular calcium into alveolar epithelial cells, cultured pneumocytes were incubated with a physiological buffer, final pH of 7.2, consisting of the following (in mM): NaCl (125), KCl (5), $KH_2PO_4$ (1.2), $CaCl_2$ (2.0), HEPES (25), glucose (6), $MgSO_4$ (1.2). For experiments conducted in the absence of extracellular calcium, cells were maintained in nominal calcium buffer containing (in mM) NaCl (125), KCl (3), $KH_2PO_4$ (1.2), HEPES (25), $MgSO_4$ (1.2), and $MgCl_2$ (3.8). During the course of experiments requiring calcium-free incubations, ethylene glycol-bis-tetraacetic acid (EGTA) was added to the nominal-$Ca^{2+}$ buffer at a final concentration of 1 mM to remove residual extracellular calcium. A the end of calcium-free incubations, restoring the nominal-$Ca^{2+}$ buffer to calcium-sufficient levels was performed by addition of 3 mM $CaCl_2$. A the end of all experiments, the calcium ionophore ionomycin was added as a positive control to insure that the Fura-2 indicator was responding to changes in intracellular free calcium.

Therefore in order to study the structure/activity relationship of the DiHOxyEDEs, they were purified and tested for their ability to trigger a rise in intracellular free $Ca^{2+}$. Intriguingly, the cis DiHOxyEDEs (at 50 $\mu$M) were found to be much more potent than the trans-DiHOxyEDEs in causing a rise in intracellular $Ca^{2+}$. The cis DiHOxyEDEs caused a rise in $Ca^{2+}$ that was anywhere from 23% to 161% greater than resting levels 5 minutes after exposure. However the trans DiHOxyEDEs only caused a very small rise of intracellular free $Ca^{2+}$ anywhere from 0% to 11% above resting free $Ca^{2+}$ levels, after 5 minutes following exposure to the DiHOxyEDEs. Therefore there was a significant difference in the biological potency between the cis and trans stereoisomers of these novel AA metabolites. Bioactive efficacy was also dependent on the placement of, the tetrahydrofuran-diol group along the carbon chain. Location of the cis tetrahydrofuran-diol moiety on either end of the carbon chain resulted in a reduction in DiHOxyEDE ability to trigqer a rise in intracellular $Ca^{2+}$; i.e., mid-chain oxidation augmented the potency. As earlier noted, Table 1 summarizes the structures of the novel, biologically active arachidonic acid metabolites.

Calcium ion has long been known as an important physiological regulator. Many cells respond to extracellular stimuli by altering their intracellular calcium concentration, which in turn exerts biochemical changes either by itself or through its interaction with calmodulin. In many nerve and muscle cells the activation of adenylate cyclase results in an influx of extracellular calcium. cAMP activates a voltage-dependent calcium channel in the presynaptic nerve membrane, allowing calcium ions to flow in and triggering synaptic transmission. The calcium influx in muscle cells triggers muscle contraction and is responsible for the increased rate and force of heartbeats caused by $\beta$-adrenergic agonists. Within the gas exchange region of adult mammalian lung, alveolar epithelium provides the principal resistance to the movement of water and solutes across the air-blood barrier and into the air spaces of alveoli, hence, preventing pulmonary edema. Altering intracellular concentrations of calcium in pulmonary epithelial cells can alter their ability to maintain epithelial barrier function and surfactant production.

Both enzymes involved in the biogenesis of DiHOEDEs, which we have demonstrated to be endogenous metabolites capable of causing calcium influx, are inducible by a variety of drugs and pesticides. Our in vitro studies have shown that synthetic mixtures of methyl DiHOEDEs can rapidly elevate intracellular calcium levels in isolated pulmonary epithelial cells. Mixture of the precursor methyl DiEpEDEs elevated intracellular calcium levels at a significantly lower rate. After purifying the mixture of methyl DiHOEDE isomers we observed that some of these regio- and positional isomers were more potent than others and some were inactive in the intracellular calcium influx assay (see Table 1).

Because DiHOEDEs are bioactive and their biogenesis is inducible, these novel metabolites should be viewed as important chemical mediators able to alter cellular homeostasis.

Therefore, discovery of these biologically active eicosanoids uncovers yet another important chemical mediation pathway which is influenced by xenobiotics and is capable of elevating intracellular concentrations of calcium. This pathway potentially can serve as a point for pharmacological intervention to influence certain biological events. Finally, DiHOEDEs may represent a valuable group of biochemical tools for carrying out calcium (and other ions) related experiments.

Thus, due to their biological activity, these compounds have a variety of uses. For example, like the leukotoxins and their diols they can be used as diagnostic and clinical research tools and antibodies can be raised against them. Once antibodies are made to linoleate or arachidonate oxylipins they can be used to monitor these compounds in specific tissues by immunohistological techniques.

Polyclonal antibodies have been raised against DiHOxyEDEs and other oxylipins using the following described methodology. That is, such antibodies have been and generally are raised in animals by multiple subcutaneous (sc) or intraperitoneal (ip) injections of the hapten and an adjuvant. It may be useful to conjugate the compounds to a protein which is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxy-succinimide (through lysine residues), glutaraldehyde, succinic anhydride, $SOCl_2$, or $R^1N=C=NR$. Coupling can be through the C-1 acid, diol, or preferably through an $\omega$-carbon linker exposing the major functional groups. A metabolite of the oxylipin can be used as a hapten. For example the beta-glucuronide metabolite of the diol of leukotoxin has been prepared for this use. Different handles in heterologous assays will increase assay sensitivity.

Animals can be immunized against the immunogenic conjugates or derivatives by combining 0.1 mg of conjugate, for rabbits or mice with Freund's complete adjuvant and injecting the solution s.c. in multiple sites (rabbits) or i.p. for mice. One month later the animals are boosted. Seven to fourteen days later animals are bled and the serum is assayed for anti-hapten titer. Animals are boosted until the titer plateaus. Preferably, the titer is checked with a conjugate of the same hapten, but conjugated to a different protein and/or through a different cross-linking agent. Also, aggregating agents such as alum are used to enhance the immune response.

Monoclonal antibodies are prepared by recovering spleen cells from immunized animals and immortalizing the cells in conventional fashion, e.g. by fusion with myeloma cells or by EB virus transformation and screening for clones expressing the desired antibody.

Such antibodies are useful in diagnostic assays. In one embodiment of a receptor binding assay, an antibody composition which binds to all of a selected plurality of members of the novel compounds is immobilized on an insoluble matrix, the test sample is contacted with the immobilized antibody composition in order to adsorb all the compounds, and then the immobilized compounds are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

Such antibodies also are useful for affinity purification of culture or natural sources or from recombinant cells. The antibodies and resulting immunodiagnostics for leukotoxins and leukotoxin diols are useful for predicting susceptibility of ARDS and related disorders, progress of the disease, and for monitoring success of the therapy. Immunodiagnostics for tetrahydrofuran diols are useful for monitoring disease progress and therapy, for instance, in diabetes and inflammatory disorders.

EXAMPLE 1

Polyclonal Antibodies to the Arachidonic Acid THF-Diol Metabolites

Hapten: A mixture of the THF-diols of arachidonic acid (AATHF-diols; compounds 1–12 in Table 1) was used as the hapten for the development of antibodies.

Coupling Chemistry: The hapten was coupled to various proteins through the carboxylic acid group. The carboxylic acid of the AATHF-diols was activated using N-hydroxysulfosuccinimide and 1-ethyl-3-(3-dimethylaminopropyl)carbodiimide (EDC). The activated AATHF-diols were then reacted with various protein solutions (bovine serum albumin, BSA; ovalbumin, OVA; conalbumin, CONA; keyhole limpet hemocyanin, KLH) to yield the following protein conjugates (coating antigens):

BSA-AATHF-diols
OVA-AATHF-diols
CONA-AATHF-diols
KLH-AATHF-diols
239A30-AATHF-diols 239A30 is ovalbumin that has had free amino groups modified with 1,3-diaminopropane, providing a spacer between the protein surface and the conjugated hapten. All conjugates were purified by extensive dialysis and stored at −20° C.

Immunization of Rabbits: The KLH-AATHF-diols and 239A30-AATHF-diols were used to immunize rabbits. Polyclonal antibodies were raised in female New Zealand white rabbits (3–5 kg). Antigens were emulsified in Freund's complete adjuvant and administered intradermally to the back. In a typical immunization protocol, the rabbits were injected intradermally with 100 $\mu$g antigen on day 1. After one month, the rabbits were boosted with an additional 50–100 $\mu$g of antigen in Freund's incomplete adjuvant and 10–15 mL blood taken from the ear vein 10 days later. Serum was isolated by centrifugation, sodium azide added as a preservative (0.02%), then aliquoted and stored at −20 or −80° C. The serum was screened for recognition of the analyte. Since antibodies to AATHF-diols were obtained, boosting and bleeding, as above, continued on a monthly basis. Rabbits were exsanguinated after the fourth boost. Characterization of the antibodies was conducted on this final bleed.

Screening of Rabbit sera for Binding to the Coating Antigens Produced Above: To determine if the antisera produced could bind the AATHF-diols, a checkerboard titration was conducted where each rabbit serum was screened against the various coating antigens produced above. The checkerboard titrations were conducted using an indirect enzyme linked immunosorbent assay. Briefly the coating antigens were coated to the wells of a 96 well microtiter plate in high pH buffer using passive adsorption. Each coating antigen was tested at several concentrations. After a wash step, different dilutions of the antibody were added to each well. After an incubation, a second antibody (goat anti-rabbit IgG conjugated to alkaline phosphatase) was added and incubated at room temperature. After a wash step, the bound antibodies were detected by the conversion of p-nitrophenylphosphate substrate to p-nitrophenol.

The resulting antisera bound well to the BSA-AATHF-diol and the OVA-AATHF-diol coating antigens. The CONA-AATHF-diol coating has not yet been tested. Subsequent screening showed that antibody 935 (anti-KLH-AATHF-diol) bound well to 239A30-AATHF-diol.

Screening ELISA for Solvent Stability: Due to the possibility of solubility problems with the analyte, DMSO was chosen to improve solubilization while limiting any negative effects of solvent on the antibody. Thus, the first studies screened antibody binding and inhibition by AATHF-diols in the presence of varying concentrations of DMSO. Between 10 and 25% DMSO gave no significant decrease in the maximum signal generated in the absence of analyte. The relative inhibition by AATHF-diols was also unchanged. Thus 25% DMSO was used in subsequent experiments.

Competitive Enzyme Immunoassay: A standard indirect competitive ELISA format was used to detect AATHF-diols. Briefly, the wells of a 96 well microtiter plate were coated with 239A30-AATHF-diol by passive adsorption. After a wash, the analyte (AATHF-diols or other structurally related compounds) was added, followed by the anti-AATHF-diols antibody (#935). After a one hour incubation, the unbound materials were removed from the well by a wash step. The second antibody (goat anti-rabbit IgG conjugated to alkaline phosphatase) was added to each well and incubated for one hour. Unbound materials were washed away and the substrate added. The production of colored product was inversely proportional to the amount of analyte present in the well.

Inhibition in the Competitive Enzyme Immunoassay by Arachidonic Acid Metabolites and Other Structurally Related Compounds: This system (coating with 239A30-AATHF-diols, 1 $\mu$g/mL; antibody 935 diluted 1/1000; prepare analyte in a final concentration in the well of 25% DMSO) was used to conduct screens for inhibition by various arachidonic acid metabolites and other structurally related compounds (see Table 3 below).

TABLE 3

Inhibition by various arachidonic acid metabolites and other structurally related compounds

| Compound | % Inhibition at 100 pg/μL Experiment #1 | % Inhibition at 100 pg/μL Experiment #2 |
|---|---|---|
| AATHF-diols—free acid (1,2)[a] | 60 | 63 |
| AATHF-diols—methyl ester (1,2) | 75 | 77 |
| AATHF-diols—free acid, hydrogenated[b] | 4 | |
| Eico THF-diol—free acid (11,12,5,6) | 52 | 51 |
| Eico THF diol—methyl ester (11,12,5,6) | | 56 |
| Linoleic acid THF-diols—free acid | 29 | 49 |
| Linoleic acid THF-diols—methyl ester | | 34 |
| DEED, methyl ester | 0 | |
| Methyl linoleate diepoxides | 0 | |

[a]Numbers in parentheses are the compound number from Table 1.
[b]These compounds are the same as compounds 1 and 2 only lacking the double bonds.

In the first experiment the concentrations tested were 1, 100, 10 000 and 1 000 000 pg/μL. In the second experiment the concentrations tested were $10^{-6}$ pg/μL, $10^{-4}$ pg/μd, 0.01, 1, 100, 10 000 and 1 000 000 pg/μL Although the expected sigmoidal shaped curves were obtained for most of the compounds, the concentration range was too wide to precisely calculate an IC50 (often used as an indicator of sensitivity). Thus the data reported here are noted as percent inhibition at 100 pg/μL.

Where the same compound was tested in the two experiments, the inhibitions at 100 μg/μL were remarkably similar, indicating in this screen that these antibodies can recognize THF-diols of arachidonic acid, linoleic acid and eicosadienoic acid in both the free acid and methyl ester forms.

EXAMPLE 2

Mice were administered (intravenous injection) leukotoxin/iso-leukotoxin (400 mg/kg) or leukotoxin/iso-leukotoxin diols (400 mg/kg) through tail vein. The mice given leukotoxin/iso-leukotoxin diols died of respiratory distress in 5 minutes after the injection, while the animals given leukotoxin/iso-leukotoxin survived.

In sum, we have demonstrated that leukotoxin diol acts more quickly and is more toxic than leukotoxin in a variety of cells, such as rat alveolar epithelium, human bronchiolar epithelium (HeLa) and cardiac muscle. Intravenous injections of leukotoxin diol (300 mg/kg) rapidly induce ARDS like symptoms such as pulmonary edema, difficulty in breathing and multiple organ failure. Within one hour of exposure to leukotoxin diol, both murine liver and lung show dramatic signs of cellular necrosis. These two organs are also the first to fail in ARDS. These unexpected results are particularly surprising since epoxide hydrolase is normally thought of as a detoxification enzyme. Accordingly, in one aspect the present invention is applied to treat inflammatory disease, particularly ARDS, by providing methods for screening inhibitors of epoxide hydrolase and by admininstering therapeutic amounts of epoxide hydrolase inhibitors to patients. Yet further, because we have discovered that novel DiHOxyEDEs are biomarkers of inflammation, another aspect of the invention is to make antibodies to linoleate or arachidonate oxylipins that are usefully monitored in tissues by immunohistological techniques.

It is to be understood that while the invention has been described above in conjunction with preferred specific embodiments, the description and examples are intended to illustrate and not limit the scope of the invention, which is defined by the scope of the appended claims.

It is claimed:

1. An isolated tetrahydrofuran diol of arachidonic acid (DiHOxyEDE), said DiHOxyEDE having a tetrahydrofuran ring and bearing hydrocarbon substituents at positions 2,5 of the tetrahydrofuran ring, said DiHOxyEDE having biological activity.

2. The DiHOxyEDE of claim 1, wherein the biological activity causes a rise in intracellular free $Ca^{2+}$ in rat pulmonary alveolar cells.

3. The DiHOxyEDE of claim 1 wherein the 2,5 substituents are in a cis stereoconfiguration or the DiHOxyEDE is a racemic mixture.

4. The DiHOxyEDE of claim 3, wherein the 2,5 hydrocarbon substituents are each $C_4$–$C_{12}$ alkyl or alkenyl with a hydroxyl group on one substituent and a carboxyl group distal from the hydrofuran ring on the other substituent, or having both a hydroxyl group and a distal carboxyl group on one of the substituents.

5. A method of preparing said isolated tetrahydrofuran diol of arachidonic acid of claim 4 wherein the diol as a metabolic product is obtained from digestion with soluble epoxide hydrolase.

6. A method of preparing said isolated tetrahydrofuran diol of arachidonic acid of claim 1 wherein the diol is derived from a diepoxide of arachidonic acid.

7. The compound methyl cis-9,12-dihydroxy-8(11)-oxy-5(Z),14(Z)-eicosadienoate or racemic mixtures of said compound.

8. The compound methyl cis-12,15-dihydroxy-11(14)-oxy-5(Z),8(Z)-eicosadienoate or racemic mixtures of said compound.

* * * * *